United States Patent [19]

Pawloski

[11] 4,224,318
[45] Sep. 23, 1980

[54] 3,5,6-TRIFLUORO-2-PYRIDINYL PHOSPHORUS COMPOUNDS

[75] Inventor: Chester E. Pawloski, Bay City, Mich.

[73] Assignee: The Dow Chemical Company, Midland, Mich.

[21] Appl. No.: 965,543

[22] Filed: Dec. 1, 1978

[51] Int. Cl.² ............................. C07F 9/58; A01N 9/36
[52] U.S. Cl. ......................................... 424/200; 546/25
[58] Field of Search ............................ 546/25; 424/200

[56] References Cited

U.S. PATENT DOCUMENTS

| | | | |
|---|---|---|---|
| 3,244,586 | 4/1966 | Rigterink | 546/25 |
| 3,478,037 | 11/1969 | Fest et al. | 546/25 |
| 3,810,902 | 5/1974 | Rigterink | 546/25 |
| 3,972,887 | 8/1976 | Freedman | 546/25 |
| 4,115,557 | 9/1978 | Pawloski | 546/25 |

FOREIGN PATENT DOCUMENTS 2513745  10/1975  Fed. Rep. of Germany ............. 546/25

*Primary Examiner*—Alan L. Rotman
*Assistant Examiner*—Natalia Harkaway
*Attorney, Agent, or Firm*—S. Preston Jones; Ronald G. Brookens

[57] ABSTRACT

Compounds are prepared which correspond to the formula

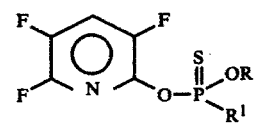

wherein R represents alkyl of 1 to 4 carbon atoms and R¹ represents OR, phenyl or ethyl. These compounds have been found to be highly active in the kill and control of soil insects.

8 Claims, No Drawings

3,5,6-TRIFLUORO-2-PYRIDINYL PHOSPHORUS COMPOUNDS

SUMMARY OF THE INVENTION

The compounds of the present invention are trifluoro pyridinyl phosphorothioates which correspond to the formula

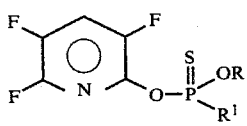

wherein R represents alkyl of 1 to 4 carbon atoms and $R^1$ represents OR, phenyl or ethyl.

In the present specification and appended claims the phrase alkyl of 1 to 4 carbon atoms is employed to designate straight or branched chain alkyl groups containing from 1 to 4 carbon atoms.

The compounds of the present invention are oily liquids or solids at ambient temperatures and are soluble in many common organic solvents, such as, for example, carbon tetrachloride, acetone, toluene, methylene chloride, dimethylformamide and the like and are of low solubility in water. These compounds have exceptional activity in the kill and control, when used in insecticidally-effective amounts, of soil insects especially the larvae of the western spotted cucumber beetle. These active compounds may be formulated with the usual insecticide carriers, well known to those skilled in the art, to provide insecticidal compositions for the above use.

The compounds of the present invention can be prepared by the reaction of an alkali metal salt of 3,5,6-trifluoro-2-pyridinol with an appropriate phosphorochloridothioate in the presence of an inert organic solvent. This reaction can be characterized as follows:

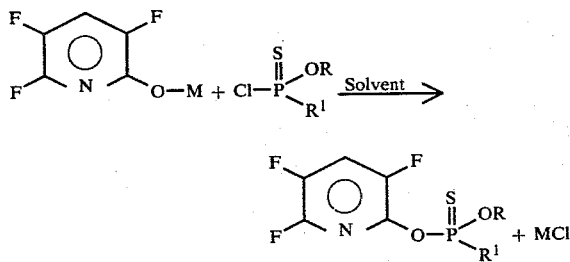

wherein R and $R^1$ are as hereinbefore set forth and M represents sodium, potassium, lithium or cesium. No attempt has been made to present a balanced equation. If desired, the reaction can be carried out in the presence of a catalyst.

In carrying out the above process, the alkali metal salt is usually prepared first by providing a mixture of the pyridinol starting material, alkali metal carbonate, and the solvent. This mixture is heated at from about 25° C. to about 50° C., with agitation, until formation of the alkali metal salt of the pyridinol takes place, usually from about 1 to about 2 hours. At this time, the appropriate phosphorus reactant is added thereto. The resulting reaction mixture is maintained at about 15° C. to about 100° C., with agitation, until the reaction is substantially complete, usually from about 1 to about 8 hours.

Upon completion of the reaction, the product mixture is cooled, the insolubles filtered therefrom and the solvent is removed. The residue is taken up with a solvent such as methylene chloride and washed with water. The methylene chloride layer is dried, filtered and distilled under reduced pressure to remove the solvent therefrom. The resulting product can be used as prepared, however, if desired, it can be further purified by conventional techniques known to those skilled in the art.

Ordinarily, substantial equimolar proportions of the pyridinol and phosphorus reactants and the alkali metal carbonate are employed. However, the alkali metal carbonate and the pyridinol starting material can be employed in slight excess of the stoichiometric requirements in order to insure the obtainment of the highest yields.

Catalysts useful in carrying out the present process include tertiary amines having a pKa of at least about 9.5 as taught in U.S. Pat. No. 3,928,370; co-catalyst which are mixtures of quaternary ammonium as phosphonium salts and organic teritary amines such as taught in U.S. Pat. Nos. 3,907,815; 3,917,621; 4,007,197 and 4,016,225 which includes quaternary ammonium compounds such as tetraalkyl ammonium salts, such as tetra-n-butyl-, tetrahexyl-, tri-n-butyl methyl-, cetyl trimethyl-, trioctyl methyl- and tridecyl methyl ammonium chlorides, bromides, bisulfates, tosylates, etc.; arylalkyl ammonium salts, such as tetrabenzyl-ammonium chloride, benzyl trimethyl-, benzyl triethyl-, benzyltributyl-, and phenethyl-trimethylammonium chlorides, bromides, etc.; arylammonium salts, such as triphenyl methyl ammonium fluoride, chloride or bromide, N,N,N-trimethylanilinium bromide, N,N-diethyl-N-methylanilinium bisulfate, trimethyl naphthyl ammonium chloride, p-methylphenyl trimethyl ammonium chloride or tosylate, etc.; 5- and 6-membered hetrocyclic compounds containing at least one quaternized nitrogen atom in the ring, such as N-methylpyridinium chloride or methyl sulfate, N-hexyl pyridinium iodide, (4-pyridyl)-trimethylammonium chloride, 1-methyl-1-azabicyclo[2.2.1]heptane bromide, N,N-dibutylmorpholinium chloride, N-ethylthiazolium chloride, N-butylpyrrolium chlorides, and the like; additionally, mercuric chloride and other such materials known for use in similar preparative procedures can also be employed.

DESCRIPTION OF THE PREFERRED EMBODIMENTS

The following examples illustrate the present invention and the manner by which it can be practiced but as such should not be construed as limitations upon the overall scope of the same.

EXAMPLE 1

O,O-Diethyl O-(3,5,6-trifluoro-2-pyridinyl) phosphorothioate

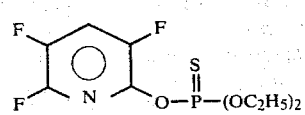

A mixture of 7.0 grams (g) (0.047 mole (m)) of 3,5,6-trifluoro-2-pyridinol, 7.0 g (0.05 m) of potassium carbonate, 0.1 g of HgCl$_2$ and 100 milliliters (ml) of acetonitrile was stirred at 50° C. for one hour. The mixture was cooled to ice bath temperatures while 7.5 g (0.042 mole) of O,O-diethyl phosphorochloridothioate was added in one portion. The mixture was heated at 40°–45° C. for three hours and thereafter allowed to cool to room temperature. The insolubles were filtered off and the liquid phase distilled under reduced pressure at 40° C. until all the solvent was removed. The resulting oil was taken up in 300 mls of methylene chloride and washed three times with 150 ml portions of water. The methylene chloride layer was dried over sodium sulfate, filtered and distilled under reduced pressure at 40° C. until all the solvent was removed. The product was an oil, and had a refractive index of n25/D=1.4726. The structure of the product was confirmed by NMR analysis. (Compound 1).

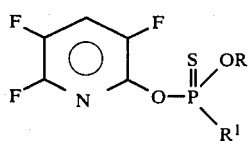

| Compound No. | X | R | R$^1$ | Refractive Index n 225/D = |
|---|---|---|---|---|
| 2 | S | —CH$_3$ | OCH$_3$ | 1.4834 |
| 3 | S | —CH$_3$ | OC$_2$H$_5$ | |
| 4 | S | —n-C$_4$H$_9$ | —n-C$_4$H$_9$ | |
| 5 | S | —i-C$_4$H$_9$ | —C$_2$H$_5$ | 1.4801 |
| 6 | S | —C$_2$H$_5$ | —φ | 1.5414 |

The compounds of the present invention have been found to be useful for the kill and control of the undesirable agricultural insects of the class known as soil insects, and especially in the kill and control of insects such as the larve of the western spotted cucumber beetle. The compounds are highly active and both kills the insects outright and prevents adult emergence from the juvenile forms of the insects. In such applications, the insect to be controlled and/or its habitat is contacted or treated with an insecticidally effective amount of one or more of the compounds of the present invention.

For all such uses, these compounds can be employed in unmodified form. However, the present invention embraces the use of an insecticidally-effective amount of the active ingredients in composition form with a chemically inert material known in the art as an adjuvant or carrier.

Thus, for example, compositions employing one or a combination of these active ingredients can be in the form of a liquid, a granule, or a dust; and the adjuvant employed can be any one of a plurality of materials including aromatic solvents, petroleum distillates, propellant substances, surface-active dispersing agents, light absorbers and finely-divided carrier solids.

The exact concentration of one or a combination of the compounds of the present invention in a composition thereof with an adjuvant therefor can vary; it is only necessary that one or a combination of the compounds be present in a sufficient amount so as to make possible the application of an insecticidally-effective or inactivating dosage.

Suitable adjuvants of the foregoing type are well known to those skilled in the art. The methods of applying the solid or liquid insecticidal formulations are similarly well known in the art.

The insecticidally-effective dosage desirable for effective use of preparations containing active compounds will naturally depend on various factors such as the active ingredient or ingredients chosen and the form of preparation. Moreover, the activities of the compounds of the present invention against different insects will vary slightly from compound to compound. Generally, for practical applications, one or a combination of these active ingredients can be broadly applied to the insect larvae or their habitat in compositions containing from about 0.001 percent to about 98 percent by weight of the compounds.

In the preparation of dust compositions, these compounds can be compounded with any of the finely-divided carrier solids such as pyrophyllite, diatomaceous earth, gypsum and the like. In such operations, the finely-divided carrier is ground or mixed with one or a combination of the compounds, as active agent(s), or wetted with a solution of the active agent(s) in a volatile organic solvent. Similarly, dust compositions can be compounded with various solid dispersing agents, such as fuller's earth, attaplugite and other clays. These dust compositions can be employed as treating compositions or can be employed as concentrates and subsequently diluted with additional solid dispersing agents or with pyrophyllite, diatomaceous earth, gypsum and the like to obtain the desired amount of active agent in a treating composition. Also, such dust compositions can be dispersed in water, with or without the aid of a surfactant, to form spray mixtures.

Furthermore, one or a combination of the compounds or a dust concentrate composition containing such compound(s) can be incorporated in intimate admixture with surface-active dispersing agents such as ionic and nonionic emulsifying agents to form spray concentrates. Such concentrates are readily dispersible in liquid carriers to form sprays containing the toxicant(s) in any desired amount. The choice of the dispersing agent and amount thereof employed are determined by the ability of the agent to facilitate the dispersion of the concentrate in the liquid carrier to produce the desired spray composition.

Granular formulations are usually prepared by impregnating a solution of the toxicant in a volatile organic solvent onto a bed of coarsely divided attapulgite, bentonite, diatomite, organic carriers such as ground corn cobs, walnut hulls, or the like.

In the preparation of liquid compositions, one or a combination of the products can be compounded with a suitable water-immiscible organic liquid and surface-active dispersing agent to produce an emulsifiable liquid concentrate which can be further diluted with water and oil to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil soluble and include the nonionic emulsifiers such as the polyoxyethylene derivatives of sorbitan esters, complex ether alcohols and the like. However, soil-soluble-ionic emulsifying agents such as mahogany soaps can also be used. Suitable organic liquids to be employed in the compositions include petroleum oils and distillates, toluene, liquid halohydrocarbons and synthetic organic oils.

An aerosol preparation according to the invention is obtained in the usual manner by incorporating the active substance and a solvent in a volatile liquid suitable for use as a propellant, such as the mixture of chlorine and fluorine derivatives of methane and ethane commerically available under the trademark FREON ®.

When utilizing the active ingredients of the present invention, one or a combination of the active ingredients or a composition containing such is applied to the insects or to their habitat in any convenient manner, for example, by means of hand dusters or sprayers or by simple mixing with the food to be ingested by the insects or larvae. Application to the foliage of plants is conveniently carried out with power dusters, broom sprayers and fog sprayers. In such foliar applications, the compositions to be employed should not contain any appreciable amounts of any phytotoxic diluents. In large scale operations, dusts or low volume sprays can be applied from aircraft.

EXAMPLE 2

Seventy-five grams of air-dried soil were placed in an 8-ounce container. To the soil was added sufficient volume of a 400 ppm aqueous dispersion, prepared by admixing a predetermined amount of one of the hereinafter set forth compounds, dissolved in a suitable inert solvent, with a predetermined amount of water and a predetermined amount of a surfactant, to give various predetermined concentrations of the toxicant in the soil on a soil-chemical basis. The treated soil was air-dried and thoroughly mixed. To each treated container, and control containers treated with water and surfactant alone, was added 0.5 milliliters of an aqueous suspension of the eggs of the Western spotted cucumber beetle (WSCB) (70–80 eggs of 3–4 days old). Additional treated soil was used to cover the eggs and a corn seed was placed in the soil and covered with additional treated soil. The containers were thereafter maintained under conditions conducive to the growth of the seeds and the hatching of the eggs. Ten to twelve (10–12) days after treatment, the containers and the plants therein were examined to determine the minimum concentration in parts of active compound per million parts of the ultimate dispersion necessary to give at least a 100 percent kill and control of the larvae from the hatched eggs. The results of this examination are set forth below in Table 2.

TABLE 2

| Number of active Compound | Minimum Concentration in PPM of active compound in soil to give a LC hd 100 of WSCB larvae |
|---|---|
| 1 | 1.5 |
| 2 | 2.5 |
| 5 | 1.5 |
| 6 | 1.5 |

Preparation of the Starting Materials

The 3,5,6-trifluoro-2-pyridinol starting material is prepared by reacting, in water, one molar proportion of 2,3,-5,6-tetrafluoropyridine with two molar proportions of a 20% NaOH solution. The thus-formed reaction mixture is stirred at reflux until substantial completion of the reaction, usually from about 4 to about 8 hours. The reaction mixture is thereafter cooled, and its water phase is seperated, and made acidic with a concentrated HCl solution, whereupon the resulting product is filtered as a solid. Additional product may be recovered by extracting the water phase with methylene chloride. The product layer is then seperated, dried over sodium sulfate, filtered and distilled. The desired 3,5,6-trifluoro-2-pyridinol product is a white solid, m.p. 93°–96° C.

The phosphorus starting materials, and methods of preparing the same, are well known to those skilled in the art.

What is claimed is:

1. A compound corresponding to the formula

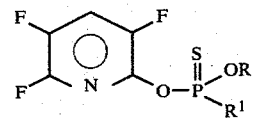

wherein R represents alkyl of 1 to 4 carbon atoms and $R^1$ represents OR.

2. A compound as defined in claim 1 wherein $R^1$ represents OR.

3. The compound of claim 2 which is O,O-dimethyl O-(3,5,6-trifluoro-2-pyridinyl) phosphorothioate.

4. The compound of claim 2 which is O,O-diethyl O-(3,5,6-trifluoro-2-pyridinyl) phosphorothioate.

5. A composition useful for the kill and control of soil insects which comprises an insecticidally effective amount of a compound corresponding to the formula

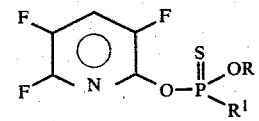

wherein R represents alkyl of 1 to 4 carbon atoms and $R^1$ represents OR in admixture with a chemically inert adjuvant therefor.

6. A composition as defined in claim 5 wherein $R^1$ represents OR.

7. The composition as defined in claim 6 wherein the compound is O,O-dimethyl O-(3,5,6-trifluoro-2-pyridinyl) phosphorothioate.

8. The composition as defined in claim 6 wherein the compound is O,O-diethyl O-(3,5,6-trifluoro-2-pyridinyl) phosphorothioate.

* * * * *